(12) United States Patent
Mecking et al.

(10) Patent No.: US 10,301,400 B2
(45) Date of Patent: May 28, 2019

(54) METHOD OF MAKING A FUNCTIONALIZED ELASTOMER

(71) Applicant: The Goodyear Tire & Rubber Company, Akron, OH (US)

(72) Inventors: Stefan Mecking, Constance (DE); Margaret Flook Vielhaber, Kent, OH (US); Hannes Leicht, Constance (DE); Julia Katharina Bauer, Pfullendorf (DE); Inigo Gottker genannt Schnetmann, Constance (DE)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 15/677,479

(22) Filed: Aug. 15, 2017

(65) Prior Publication Data
US 2019/0055325 A1    Feb. 21, 2019

(51) Int. Cl.
C08F 4/638    (2006.01)
C08F 36/04    (2006.01)
(Continued)

(52) U.S. Cl.
CPC ............ *C08F 4/6383* (2013.01); *C08F 4/545* (2013.01); *C08F 36/04* (2013.01); *C07D 209/82* (2013.01);
(Continued)

(58) Field of Classification Search
None
See application file for complete search history.

(56) References Cited

U.S. PATENT DOCUMENTS 6,693,160 B1    2/2004    Halasa
6,753,447 B2    6/2004    Halasa
(Continued)

FOREIGN PATENT DOCUMENTS

EP    3181593 A1    6/2017

OTHER PUBLICATIONS

Controlled trans-Stereospecific Polymerization of Isoprene with Lanthanide(III) Borohydride/Dialkylmagnesium Systems: The Improvement of the Activity and Selectivity, Kinetic Studies, and Mechanistic Aspects, Journal Polymer Science: Pary A: Polymer Chemistry, vol. 45, 2400-2409 (2007).
(Continued)

*Primary Examiner* — Catherine S Branch
(74) *Attorney, Agent, or Firm* — John D. DeLong

(57) ABSTRACT

The present invention is directed to a method of making a functionalized elastomer, comprising the step of polymerizing monomers comprising a conjugated diene monomer in the presence of a lathanide-based coordination polymerization catalyst activated with a magnesium compound of formula 1

$$Q-R^1-Mg-R^1-Q \qquad 1$$

where $R^1$ is phenylene, or a linear or branched alkane diyl group containing 2 to 10 carbon atoms, or a combination of one or more phenylene groups and one or more linear or branched alkane diyl groups containing 1 to 10 carbon atoms;

Q is of formula 2 or 3

$$-S-R^2 \qquad 2$$

where $R^2$ is phenyl, or a linear or branched alkyl group containing 2 to 10 carbon atoms;
(Continued)

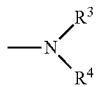

where $R^3$ and $R^4$ are independently phenyl or a linear or branched alkyl group containing 1 to 10 carbon atoms, or $R^2$ and $R^3$ taken together with the nitrogen atom represent a nitrogen containing heterocyclic group containing from 4 to 12 carbon atoms.

10 Claims, 6 Drawing Sheets

(51) Int. Cl.
| | | |
|---|---|---|
| *C08F 4/54* | (2006.01) | |
| *G01R 33/46* | (2006.01) | |
| *C07F 3/02* | (2006.01) | |
| *C07D 233/00* | (2006.01) | |
| *C07D 209/82* | (2006.01) | |

(52) U.S. Cl.
CPC .............. *C07D 233/00* (2013.01); *C07F 3/02* (2013.01); *G01R 33/46* (2013.01)

(56) References Cited

U.S. PATENT DOCUMENTS

| | | |
|---|---|---|
| 6,812,307 B2 | 11/2004 | Halasa |
| 6,825,306 B2 | 11/2004 | Halasa |
| 6,901,982 B2 | 6/2005 | Halasa |
| 6,933,358 B2 | 8/2005 | Halasa |
| 6,936,669 B2 | 8/2005 | Halasa |
| 6,995,224 B2 | 2/2006 | Halasa |
| 7,041,761 B2 | 5/2006 | Halasa |
| 7,081,504 B2 | 7/2006 | Rachita |
| 7,906,593 B2 | 3/2011 | Halasa |
| 8,492,573 B2 | 7/2013 | Thuilliez |
| 8,598,286 B1 | 12/2013 | Flook et al. |
| 8,865,829 B2 | 10/2014 | Nebhani |
| 8,993,669 B2 | 3/2015 | Nebhani |
| 9,045,627 B2 | 6/2015 | Du |
| 9,186,933 B2 | 11/2015 | Nebhani |
| 9,315,654 B1 | 4/2016 | Nebhani |
| 2016/0177008 A1 | 6/2016 | Flook |
| 2016/0177009 A1 | 6/2016 | Flook |
| 2016/0177010 A1 | 6/2016 | Flook |
| 2016/0177012 A1 | 6/2016 | Flook |

OTHER PUBLICATIONS

European Patent Office Search Report, dated Jan. 3, 2019.
Fanny Bonnet et al, Stereospecific Polymerization of Isoprene with Nd(BH4)3(THF)3 /MgBu2 as Catalyst, Stereospecific Polymerization of Isoprene with Nd(BH4)3(THF)3 /MgBu2 as Catalyst, Apr. 1, 2004 (Apr. 1, 2004), pp. 873-877, vol. 25, No. 8, Macromolecular Rapid Communications, Cedex, FR.
Hannes Leicht et al, Stereoselective Copolymerization of Butadiene and Functionalized 1,3-Dienes, Stereoselective Copolymerization of Butadiene and Functionalized 1,3-Dienes, Jun. 9, 2016 (Jun. 9, 2016), 777-780, vol. 5, No. 6, ACS Macro Letters, Konstanz, DE.
Pelletier et al., Synthesis of New Dialkylmagnesium Compounds by Living Transfer Ethylene Oligo- and Polymerization with Lanthanocene Catalysts, Angewandte Chemie, International Edition, Sep. 6, 1996, pp. 1854-1856, vol. 35, No. 16.

METHOD OF MAKING A FUNCTIONALIZED ELASTOMER

BACKGROUND OF THE INVENTION

To produce stereoregular polymers, catalytic insertion polymerization is the method of choice. Resulting stereoregular poly(1-olefins) and poly(dienes) are of enormous practical importance. An introduction of polar groups in such stereoregular polymerizations is challenging, however, due to the sensitivity of most catalysts towards heteroatom-containing substrates. An introduction of polar and reactive groups in the polymer backbone and into the end-groups in particular is desirable to enhance the compatibility with polar surface, like e.g. metals or fillers and for cross-linking. Concerning an incorporation into the polymer chain, recent work has resulted in an advance towards stereoregular polar functionalized poly(propylene) (Nozaki et al., *Angew. Chem., Int. Ed.* 2016, 55, (26), 7505-7509.) For poly(dienes), insertion polymerization of functionalized dienes and other pathways to stereoregular poly(dienes) have been reported (Leicht et al., S. ACS Macro Lett. 2016, 5, (6), 777-780; Leicht et al., Polym. Chem. 2016; Cui et al., Polym. Chem. 2016, 7, (6), 1264-1270.) Examples for syntheses of chain-end functionalized poly(dienes) are so far based on methods like anionic polymerization (Quirk et al., Polymer 2004, 45, (3), 873-880; Stewart et al., British Polymer Journal 1990, 22, (4), 319-325.) or ring opening metathesis polymerization (Hillmyer et al., Macromolecules 1997, 30, (4), 718-721; Ji et al., Macromolecules 2004, 37, (15), 5485-5489; Chung et al., Macromolecules 1992, 25, (20), 5137-5144) that do not provide access to stereoregular polymers. There remains a need for a method to produce stereoregular polymers functionalized with polar groups.

SUMMARY OF THE INVENTION

Most lanthanide-based catalyst precursors for stereoselective diene polymerization require activation by a second reagent, often organo-metal compounds. The present invention includes the usage of polar functionalized organo-metal activators for the synthesis of chain-end functionalized stereoregular dienes. Further, the combination of this method with the generation of functionalized chain-ends by quenching at the end of the polymerization and direct copolymerization with functionalized dienes gives access to stereoregular, trifunctional, hetero-telechelic poly(dienes).

The preparation of stereoregular poly(dienes) with functional groups in the main chain as well as in both end-groups, the later in a hetero-telechelic fashion is disclosed. A key element is the finding that Nd-based trans-selective systems for diene polymerization are tolerant towards different functional groups based on nitrogen or sulfur. Further, activation of $Nd(BH_4)_3 \cdot (THF)_3$ proceeds with functionalized magnesium alkyls to introduce functional groups at the initiating chain-ends. At the terminating chain-end, an end-group could be generated by conversion of reactive metal-carbon bonds present in the catalyst system with suitable quenching reagents. Notably, all three elements are compatible with one another and can be carried out together, i.e. stereoregularity or the nature of the reactive metal-polymeryl bonds are not compromised by the presence of functional activators or monomers.

Stereoregular poly(dienes) with three different functional groups were synthesized by insertion polymerization. The functional groups are located simultaneously in the polymer backbone and at both chain ends, yielding hetero-telechelic and in-chain functionalized polymers. A combination of three compatible functionalization methods allows for the syntheses of these particular polymers. $Nd(BH_4)_3 \cdot (THF)_3$ catalyzes, after activation with $MgR_2$, the direct copolymerization of 1,3-butadiene or isoprene with polar functionalized dienes, thus enabling the functionalization of the polymer's backbone. The use of functionalized organo-Mg compounds, like $(PhS-C_5H_{10})_2Mg$, for the activation of $Nd(BH_4)_3 \cdot (THF)_3$ enables the functionalization of one chain-end and quenching of the polymerization with suitable reagents like $Si(OEt)_4$ allows for the functionalization of the other chain-end. While activation of $Nd(BH_4)_3 \cdot (THF)_3$ with $MgR_2$ initiates usually a 1,4-trans selective diene polymerization, the use of polar organo-Mg compounds as activation reagents has also been shown to be a viable method for chain-end functionalization in cis-selective diene polymerizations.

The present invention therefore involves the use of functional magnesium-based chain transfer reagants that impart functionality on the end of every polymer chain. By combining this technique with known functionalization techniques such as termination with functional terminators or copolymerization with functional monomers, the invention describes a method to make stereoregular polymers that contain functionality on both ends, as well as in-chain. Either high-cis or high-trans polymers can be made through changes to the catalyst system, without affecting the functionalization reactions.

The present invention is directed to a method of making a functionalized elastomer, comprising the step of polymerizing a conjugated diene monomer in the presence of a lathanide-based coordination polymerization catalyst activated with a magnesium compound of formula 1

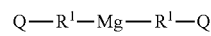

1 where $R^1$ is phenylene, or a linear or branched alkane diyl group containing 2 to 10 carbon atoms, or a combination of one or more phenylene groups and one or more linear or branched alkane diyl groups containing 1 to 10 carbon atoms; Q is of formula 2 or 3

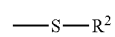

2 where $R^2$ is phenyl, or a linear or branched alkyl group containing 2 to 10 carbon atoms;

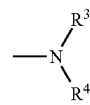

3 where $R^3$ and $R^4$ are independently phenyl or a linear or branched alkyl group containing 1 to 10 carbon atoms, or $R^2$ and $R^3$ taken together with the nitrogen atom represent a nitrogen containing heterocyclic group containing from 4 to 12 carbon atoms.

There is further disclosed a rubber composition comprising the functionalized elastomer produced by this method, and a tire comprising the rubber composition.

BRIEF DESCRIPTION OF THE DRAWINGS

FIG. 1: $^1$H NMR spectrum of a BD/3 copolymer (Table 1-A, entry 7, recorded at 27° C. in $C_6D_6$).

DETAILED DESCRIPTION OF THE INVENTION

Figure 1:
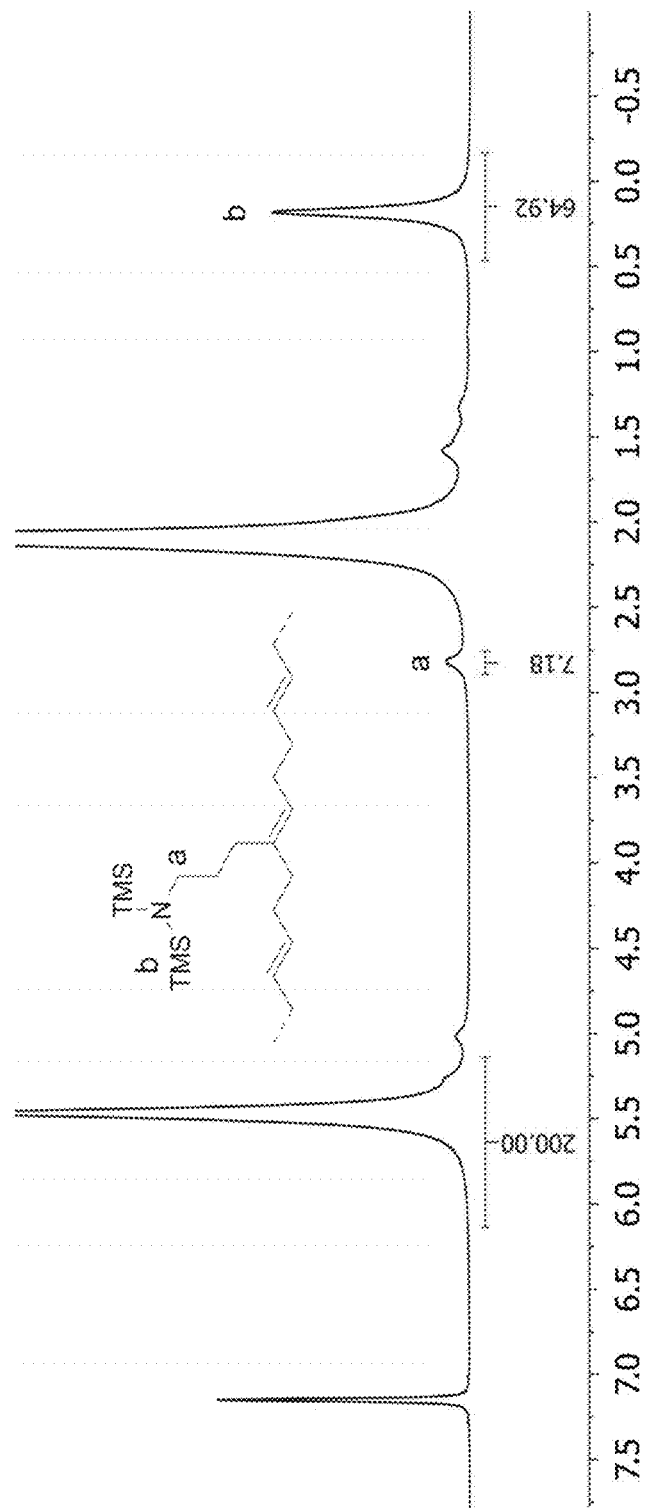
FIG. 1 shows

There is disclosed a method of making a functionalized elastomer, comprising the step of polymerizing a conjugated diene monomer in the presence of a lathanide-based coordination polymerization catalyst activated with a magnesium compound of formula 1

where $R^1$ is phenylene, or a linear or branched alkane diyl group containing 2 to 10 carbon atoms, or a combination of one or more phenylene groups and one or more linear or branched alkane diyl groups containing 1 to 10 carbon atoms;

Q is of formula 2 or 3

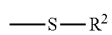

where $R^2$ is phenyl, or a linear or branched alkyl group containing 2 to 10 carbon atoms;

where $R^3$ and $R^4$ are independently phenyl or a linear or branched alkyl group containing 1 to 10 carbon atoms, or $R^2$ and $R^3$ taken together with the nitrogen atom represent a nitrogen containing heterocyclic group containing from 4 to 12 carbon atoms.

Polymerizations according to the method utilitize a lanthanide based catalyst system. Suitable catalysts include neodymium based catalysts, including neodymium borohydride complexes activated with dialkylmagnesium compounds, and neodymium carboxylates activated with dialkylmagnesium compounds and alkyl aluminum chlorides.

Such polymerizations are typically conducted in a hydrocarbon solvent that can be one or more aromatic, paraffinic, or cycloparaffinic compounds. These solvents will normally contain from 4 to 10 carbon atoms per molecule and will be liquids under the conditions of the polymerization. Some representative examples of suitable organic solvents include pentane, isooctane, cyclohexane, normal hexane, benzene, toluene, xylene, ethylbenzene, and the like, alone or in admixture.

In one embodiment, the neodymium catalyst system is a neodymium borohydride activated with a functional dialkyl magnesium compound. In one embodiment, the neodymium borohydride is $Nd(BH_4)_3 \cdot (THF)_3$ where THF is tetrahydrofuran. Suitable functional dialkyl magnesium compounds included compound of formula 1

where $R^1$ is phenylene, or a linear or branched alkane diyl group containing 2 to 10 carbon atoms, or a combination of one or more phenylene groups and one or more linear or branched alkane diyl groups containing 1 to 10 carbon atoms;

Q is of formula 2 or I3

where $R^2$ is phenyl, or a linear or branched alkyl group containing 2 to 10 carbon atoms;

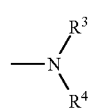

where $R^3$ and $R^4$ are independently phenyl or a linear or branched alkyl group containing 1 to 10 carbon atoms, or $R^2$ and $R^3$ taken together with the nitrogen atom represent a nitrogen containing heterocyclic group containing from 4 to 12 carbon atoms.

In one embodiment, the neodymium catalyst system used in the process of this invention is made by preforming three catalyst components. These components are (1) the functional dialkyl magnesium compound of formula I, (2) a neodymium carboxylate, and (3) an alkyl aluminum chloride. In making the neodymium catalyst system the neodymium carboxylate and the alkyl aluminum chloride compound are first reacted together for 10 seconds to 30 minutes in the presence of isoprene or butadiene to produce a neodymium-aluminum catalyst component. The neodymium carboxylate and the organoaluminum compound are preferable reacted for 2 minutes to 30 minutes and are more preferable reacted for 3 to 25 minutes in producing the neodymium-aluminum catalyst component.

The neodymium-aluminum catalyst component is then reacted with the functional dialkyl magnesium compound to yield the active catalyst system.

The neodymium catalyst system will typically be preformed at a temperature that is within the range of about 0° C. to about 100° C. The neodymium catalyst system will more typically be prepared at a temperature that is within the range of about 10° C. to about 60° C.

The neodymium carboxylate utilizes an organic monocarboxylic acid ligand that contains from 1 to 20 carbon atoms, such as acetic acid, propionic acid, valeric acid, hexanoic acid, 2-ethylhexanoic acid, neodecanoic acid, lauric acid, stearic acid and the like neodymium naphthenate, neodymium neodecanoate, neodymium octanoate, and other neodymium metal complexes with carboxylic acid containing ligands containing from 1 to 20 carbon atoms.

The concentration of the total catalyst system employed of course, depends upon factors such as purity of the system, polymerization rate desired, temperature and other factors. Therefore, specific concentrations cannot be set forth except to say that catalytic amounts are used.

Temperatures at which the polymerization reaction is carried out can be varied over a wide range. Usually the temperature can be varied from extremely low temperatures such as −60° C. up to high temperatures, such as 150° C. or higher. Thus, the temperature is not a critical factor of the invention. It is generally preferred, however, to conduct the reaction at a temperature in the range of from about 10° C. to about 90° C. The pressure at which the polymerization is carried out can also be varied over a wide range. The reaction can be conducted at atmospheric pressure or, if desired, it can be carried out at sub-atmospheric or super-atmospheric pressure. Generally, a satisfactory polymerization is obtained when the reaction is carried out at about autogenous pressure, developed by the reactants under the operating conditions used.

Examples of useful functional dialkyl magnesium compounds of formula 1 include but are not limited to compounds such as the following

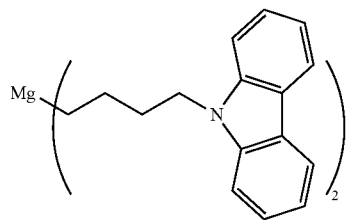

Mg-1

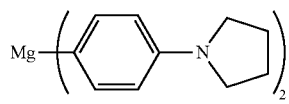

Mg-2

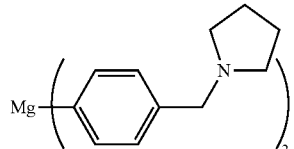

Mg-3

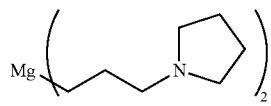

Mg-4

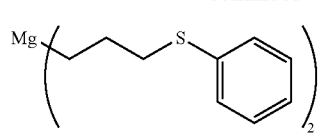

Mg-5

The polymerization can be quenched or terminated by the addition of a functional terminator, an alcohol or another protic source, such as water.

In one embodiment, the polymerization is terminated using a functional terminator. By functional terminator, it is meant an organic compound capable of terminating the polymerization reaction, wherein the organic compound is substituted with a functional group comprising at least one heteroatom selected from phosphorus, boron, oxygen, halogens and silicon.

In one embodiment, the functional terminator comprises at least one functional group selected from the group consisting of phosphane, phosphonic acid, phosphate, phosphodiester, phosphotriester, silyl, alklysilyl, alkoxysilyl, and siloxy.

Useful functional terminators include but are not limited to tetraethoxysilane, n-octyltriethoxysilane, 3-chloropropyltriethoxysilane, and chlorodiphenylphosphine.

Suitable monomers for use in the polymerization are conjugated diene monomers and functionalized versions thereof. Suitable conjugated diene monomers include 1,3-butadiene and isoprene. Other suitable conjugated diene monomers include 2,3-dimethyl-1,3-butadiene, piperylene, 3-butyl-1,3-octadiene, 2-phenyl-1,3-butadiene, and the like, and combinations thereof.

In one embodiment, the monomer includes a functionalized monomer of formula 4

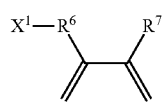

4 wherein $R^6$ is a covalent bond, phenylene, a linear or branched alkane diyl group containing 1 to 10 carbon atoms, or a combination of one or more phenylene groups and one or more linear or branched alkane diyl groups containing 1 to 10 carbon atoms; $R^7$ is hydrogen or a linear or branched alkyl group containing 1 to 10 carbon atoms; $X^1$ is selected from formulas 5 and 6

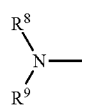

5

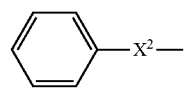

6 wherein $R^8$ and $R^9$ are independently trialkylsilyl, phenyl or a linear or branched alkyl group containing 1 to 10 carbon atoms, or one of $R^8$ and $R^9$ is hydrogen and the other is phenyl or a linear or branched alkyl group containing 1 to 10 carbon atoms, or $R^8$ and $R^9$ taken together with the nitrogen atom represent a nitrogen containing heterocyclic group containing from 4 to 12 carbon atoms; and $X^2$ is a sulfur atom or a structure of formula 7 or 8

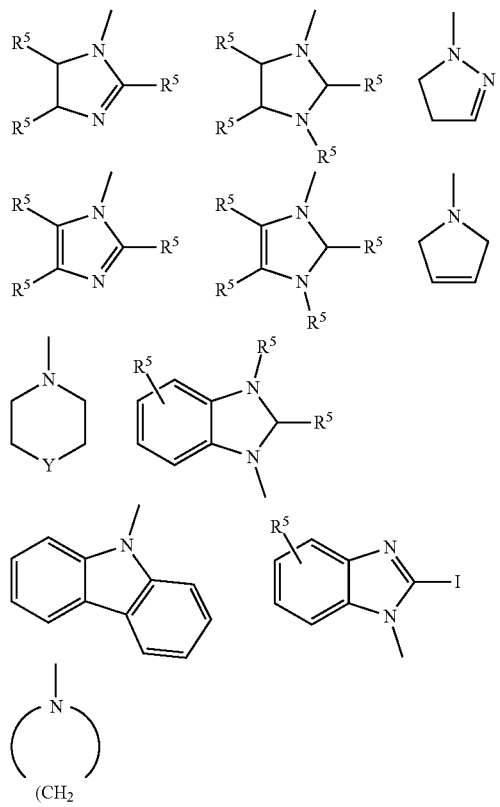

wherein when $X^2$ is of formula 8, the S atom of formula 8 is adjacent to the phenyl ring of formula 6 and the N atom of formula 8 is adjacent to $R^6$.

In one embodiment, the nitrogen containing heterocyclic group is selected from the group consisting of the structures wherein $R^5$ groups can be the same or different and represent a member selected from the group consisting of linear or branched alkyl groups containing from 1 to about 10 carbon atoms, aryl groups, allyl groups, and alkoxy groups, and wherein Y represents oxygen, sulfur, or a methylene group, and n is an integer from 4 to 12.

In one embodiment, suitable functionalized monomers are selected from the following monomer structures

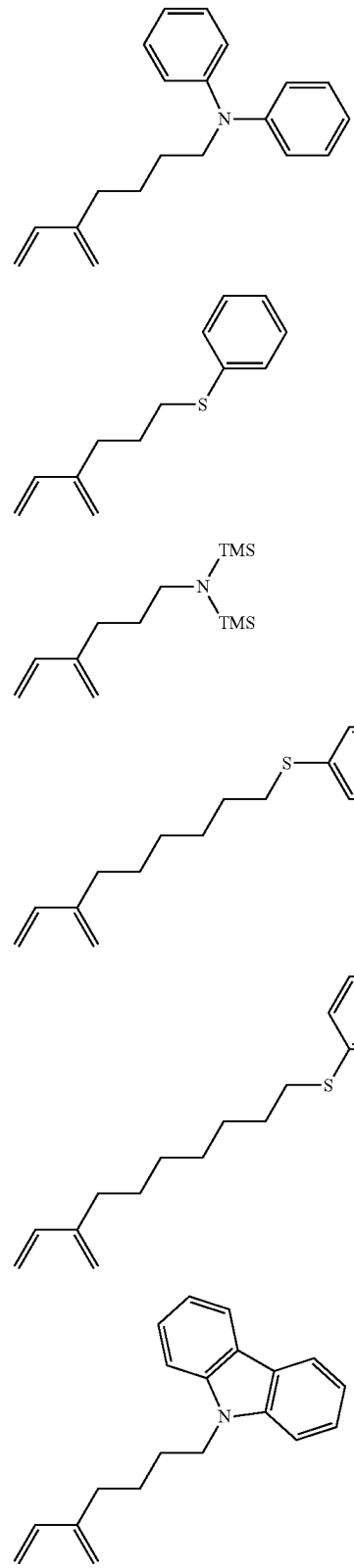

where in monomer 3, TMS refers to a trimethylsilyl group.

The use of functional magnesium-based chain transfer reagents of formula 1 imparts functionality on the end of every polymer chain end. By combining the technique with known functionalization techniques such as termination with functional terminators or copolymerization with functional monomers, the polymerization results in stereoregular polymers that contain functionality on both ends, as well as in-chain. Either high-cis or high-trans polymers can be made through changes to the catalyst system, without affecting the functionalization reactions. By stereoregular, it is meant that the polymer microstructure includes at least 80 percent by weight of monomer residues (i.e., polymer subunits derived from a given monomer) in the cis 1,4-configuration, or 90 percent by weight of monomer residues in the trans 1,4-configuration. In one embodiment, the polymer contains at least 85 percent by weight of monomer residues in cis 1,4-configuration. In one embodiment, the polymer contains at least 95 percent by weight of monomer residues in trans 1,4-configuration.

This invention is illustrated by the following examples that are merely for the purpose of illustration and are not to be regarded as limiting the scope of the invention or the manner in which it can be practiced. Unless specifically indicated otherwise, parts and percentages are given by weight.

Example 1

Homopolymerizations of BD were performed to optimize polymerization conditions for high stereoselectivity and to assess the influence of the diene:Nd ratio on the molecular weights and molecular weight distributions of the obtained polymers. 5 μmol $Nd(BH_4)_3.(THF)_3$ were activated with 1 equiv. of $MgBu_2$ in the presence of different amounts of BD in toluene (Table 1, entries 1-3). Polymerization at 60° C. for 5 h yielded in all cases highly stereoregular 1,4-trans-PBD (≥95 mol % trans-units). The molecular weights of the obtained polymers are close to the theoretically calculated molecular weights (for a polymerization where only one polymer chain per Nd is formed) and increase linearly with increasing BD:Nd ratio. Although GPC analyses indicate a bimodal molecular weight distribution (cf. SI), all molecular weight distributions are narrow ($M_w/M_n$=1.3-1.6). Hence, a controlled character of the polymerization can be assumed. DSC analyses of the polymers gave the typically two distinct melting points for high 1,4-trans-PBD. Not only butadiene but also isoprene is stereoselectively polymerized. A polymerization of isoprene in an NMR tube gives poly(isoprene) with 95% 1,4-trans units (Table 1, entry 4). The narrow molecular weight distribution and a molecular weight close to the theoretical value also indicate a controlled polymerization of isoprene. Having established the general polymerization behavior under our conditions of the catalyst system based on $Nd(BH_4)_3.(THF)_3$, three different approaches for the functionalization of the obtained stereoregular poly(diene) were explored: 1) The direct introduction of polar groups into the backbone of the polymer by insertion copolymerization of butadiene or isoprene with polar functionalized dienes. 2) The functionalization of one chain-end by reaction of the reactive metal-carbon bond with a suitable quenching reagent. 3) The functionalization of the other chain-end by using polar functionalized Mg-compounds.

TABLE 1

(Co)polymerizations of butadiene and isoprene catalyzed by $Nd(BH_4)_3 \cdot (THF)_3$ activated with $MgBu_2$.

| entry | cat. [μmol] | time [h] | diene [mmol] | comon. [μmol] | yield [mg] (%) | comon. incorp.[a] [mol %] | comon. conv. [%] | $M_n$[b] [$10^3$ g $mol^{-1}$] | $M_w/M_n$[b] | $T_m$[c] [° C.] | 1,4-trans-content[d] [%] |
|---|---|---|---|---|---|---|---|---|---|---|---|
| 1 | 5 | 5 | 4.6 BD | — | 202 (81) | — | — | 43 | 1.3 | 45/94 | 95 |
| 2 | 5 | 5 | 9.2 BD | — | 440 (89) | — | — | 89 | 1.6 | 45/98 | 97 |
| 3 | 5 | 5 | 13.8 BD | — | 698 (94) | — | — | 133 | 1.4 | 46/98 | 95 |
| 4 | 20 | 3 | 2 IP | — | 125 (92) | — | — | 7.7 | 1.5 | n.d. | 95 |
| 5[f] | 60 | 2.5 | 6 IP | — | 330 (81) | — | — | 12 | 1.5 | n.d. | 93 |
| 6[g] | 60 | 3 | 6 IP | — | 411 (99) | — | — | 5.8 | 1.3 | n.d. | 95 |

Polymerization conditions: $Nd(BH_4)_3.(THF)_3$:$MgBu_2$=1:1, T=60° C. in toluene a) determined by $^1H$ NMR b) determined by GPC in THF vs. PS standards. c) determined by DSC d) determined by $^{13}C$ NMR e) incorporation not determined because comonomer incorporation signals are overlapped by the polymer backbone. f) quenched with 600 μmol $Si(OEt)_4$. g) quenched with 600 μmol $Ph_2PCl$.

Example 2

Copolymerization with Polar Functionalized Dienes.

The functional group tolerance of $Nd(BH_4)_3.(THF)_3$ activated with $MgR_2$ in diene polymerizations was tested with comonomers 1-5 (Table 1-A, entries 7-12).

Chart 1: Polar functionalized dienes used in copolymerizations with butadiene and isoprene.

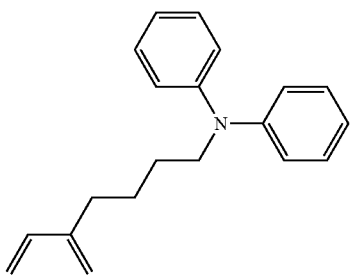

1

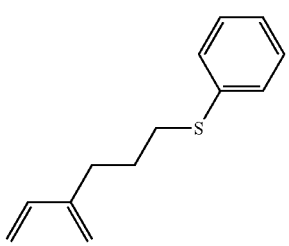

2

-continued

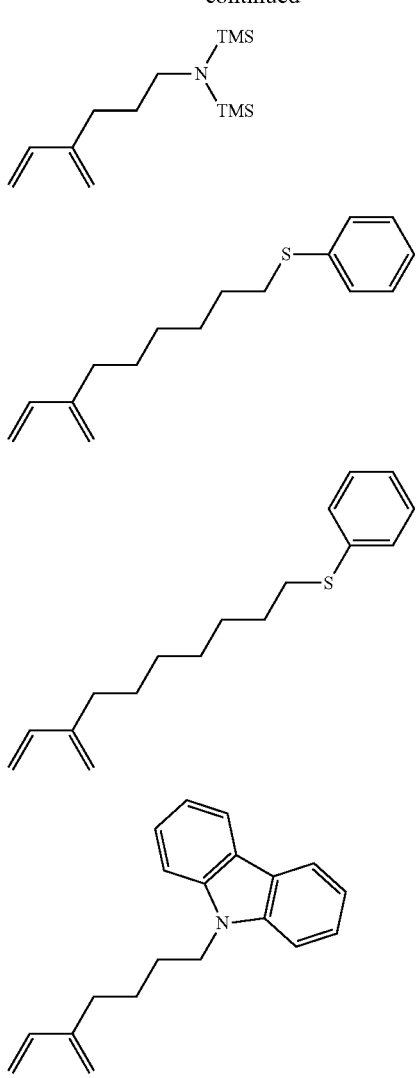

entry 1 vs. 7). Copolymerizations with 3 and 5 result in polymers with broader molecular weight distributions. Additionally, copolymers of 1 and 3 exhibit a lowered second melting point. Incorporation of 1 and 3 proceeds efficiently (73% and 99% comonomer conversion) and yields copolymers with incorporations of 3.9 mol % and 3.6 mol % respectively (FIG. 1). The incorporation ratio of the copolymer synthesized from butadiene and 2 could not be determined unequivocally because all proton signals of the propyl side chain (most indicative PhS—CH$_2$—) are overlapped by signals of the poly(butadiene) backbone (Table 1, entry 8). In contrast, the signal of the PhS—CH$_2$-group is shifted in copolymers with 4 and 5, allowing again for detection and determination of the comonomer incorporation (3.4 and 3.3 mol % Table 1, entries 11 and 12). The formation of true copolymers was, additionally to $^1$H NMR experiments, undoubtedly established by extensive NMR analyses of the polymers including 1D TOCSY, 2D and DOSY experiments.

These polymerizations prove that Nd(BH$_4$)$_3$.(THF)$_3$ activated with MgR$_2$ is a viable catalyst system for the direct copolymerization of butadiene or isoprene with functionalized dienes to polar functionalized 1,4-trans-poly(dienes).

Example 3

Chain-End Functionalization by Quenching.

The second part of the functionalization strategy aims at the reaction of reactive metal-carbon bonds present with a suitable quenching reagent (Scheme 1).

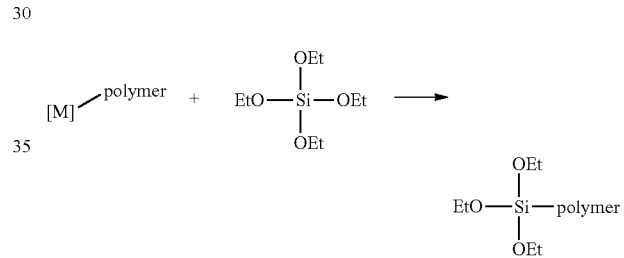

Scheme 1: Chain-end functionalization by reaction of metal-polymer carbon bonds with Si(OEt)$_4$ as reactive quenching reagents.

TABLE 1-A

| entry | cat. [μmol] | time [h] | diene [mmol] | comon [μmol] | yield [mg] (%) | comon. incorp.[a] [mol %] | comon. conv. [%] | M$_n$[b] [10$^3$ g mol$^{-1}$] | M$_w$/M$_n$[b] | T$_m$[c] [° C.] | 1,4-trans-content[d] [%] |
|---|---|---|---|---|---|---|---|---|---|---|---|
| 7 | 5 | 5 | 4.6 BD | 150 | 152 (61) | 1  3.9 | 73 | 43 | 1.8 | 50/72 | 94 |
| 8 | 5 | 5 | 4.6 BD | 170 | 195 (79) | 2  n.d.[e] | n.d.[e] | 46 | 1.6 | 48/93 | 94 |
| 9 | 5 | 5 | 4.6 BD | 150 | 222 (89) | 3  3.6 | 99 | 44 | 3.0 | 47/61 | 94 |
| 10 | 60 | 5 | 6.2 IP | 430 | 484 (92) | 3  7.2 | 99 | 7.7 | 1.3 | n.d. | 96 |
| 11 | 5 | 5 | 4.6 BD | 0.16 | 208 | 4  3.4 | 82 | 43 | 1.9 | 50/73 | 93 |
| 12 | 5 | 5 | 4.6 BD | 0.15 | 196 | 5  3.3 | 80 | 47 | 3.0 | 49/71 | 93 |

Polymerization conditions: Nd(BH$_4$)$_3$.(THF)$_3$:MgBu$_2$=1:1, T=60° C. in toluene a) determined by $^1$H NMR b) determined by GPC in THF vs. PS standards. c) determined by DSC d) determined by $^{13}$C NMR e) incorporation not determined because comonomer incorporation signals are overlapped by the polymer backbone. f) quenched with 600 μmol Si(OEt)$_4$. g) quenched with 600 μmol Ph$_2$PCl.

Figure 2:
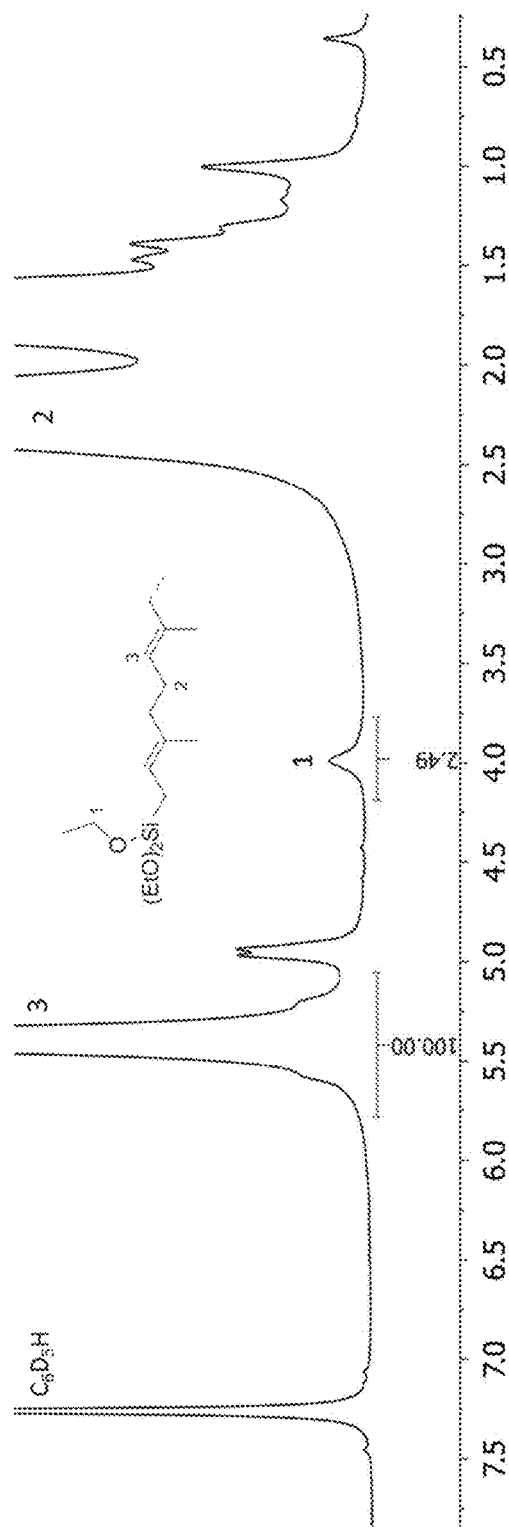
FIG. 2: $^1$H NMR spectrum of a poly(isoprene) sample with triethoxysilyl end-groups (Table 1, entry 5, recorded at 27° C. in $C_6D_6$).

Comparison of the copolymerizations with a BD homopolymerization under otherwise identical conditions reveals no to little adverse impact of the comonomer present on yield, molecular weight and stereoselectivity (e.g. Table 1, 1-A, We tested four different quenching reagents, Si(OEt)$_4$, Ph$_2$PCl, B(OEt)$_3$, and P(O)(OEt)$_3$ towards their reactivity with the aforementioned metal-carbon bonds. For this purpose, polymerizations run with an IP:Nd ratio of 100:1 were terminated by the addition of the quenching reagents (cf. Table 1, entries 5 and 6, for examples with Si(OEt)$_4$ and Ph$_2$PCl). The reaction mixture was stirred at the polymerization temperature until it became colorless. The polymers were isolated by precipitation in dry acetonitrile (polymers quenched with Si(OEt)$_4$, B(OEt)$_3$, or P(O)(OEt)$_3$) or acidified MeOH (Ph$_2$PCl-modified) followed by drying under reduced pressure. To verify the functionalization by quenching, the polymers were subjected to a thorough analysis by means of NMR spectroscopy. $^1$H and $^{13}$C NMR showed no indication for a successful functionalization for polymers quenched with B(OEt)$_3$ or P(O)(OEt)$_3$. In contrast, the polymer quenched with Si(OEt)$_4$ exhibits characteristic shifts for an ethoxy-moiety in the $^1$H NMR spectrum at δ=3.89 ppm and δ=1.20 ppm (FIG. 2). The assignment of these signals to a SiOCH$_2$CH$_3$ group is substantiated by $^1$H-$^{13}$C—HSQC NMR spectroscopy revealing the corresponding carbon shifts at δ=59.4 ppm and 17.8 ppm. A connectivity of these ethoxy moieties to the poly(isoprene) backbone was probed by 1D TOCSY and DOSY NMR spectroscopy. The formation of ethoxysilyl endgroups is unambiguously proven by DOSY-NMR. Both, the SiOCH$_2$CH$_3$ group as well as the backbone signals exhibit the same diffusion coefficient, i.e. both correlate to a species with a comparable molecular weight, this would not be the case for e.g BuSi(OEt)$_3$ which could likely be formed from the reaction of residual RMgBu with Si(OEt)$_4$.

A quantitative view on the end-group functionalization reveals that the reaction does not proceed quantitatively, with quenching efficiencies (i.e. portion of chains functionalized) between 40 and 50%.

A polymer quenched with Ph$_2$PCl at the end of the polymerization reaction exhibits characteristic $^1$H NMR shifts in the aromatic region at δ=7.81–6.90 ppm, indicating a successful functionalization of the polymer. Although this assumption is substantiated by the observation of signals in the $^{31}$P NMR spectrum, the presence of at least seven different $^{31}$P species, however, points to a low selectivity or the occurrence of side reactions. Still, DOSY-NMR establishes the connection of the aromatic protons to the poly(isoprene) backbone in terms of identical diffusion coefficients and thus a successful functionalization.

Example 4

Chain-End Functionalization by Activation with Functionalized Mg-Reagents.

The third functionalization strategy targets the introduction of functional groups via the use of functional activation reagents, i.e. organo-magnesium compounds. This functionalization would result in poly(dienes) with polar end groups (Scheme 2).

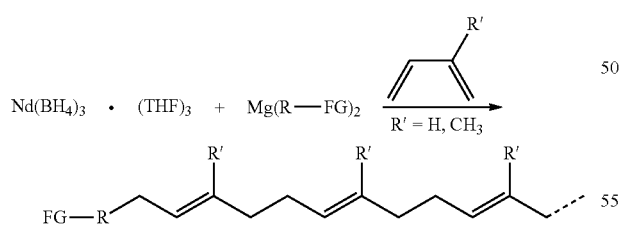

Scheme 2: Activation of Nd(BH$_4$)$_3$.(THF)$_3$ with functionalized organo-magnesium compounds gives access to chain-end functionalized poly(dienes).

Before we started to assess the potential of this approach towards a possible functionalization of the polymer chain-end, we tested our polymerization conditions in terms of this method's general ability to transfer organic moieties from Mg to Nd and eventually to the chain-end with a non-functionalized alkyl group, i.e. an n-butyl moiety through transfer from MgBu$_2$. The presence of n-butyl end-groups was observed by the appearance of a $^1$H NMR signal with a shift typical for aliphatic —CH$_3$ groups (δ=0.90 ppm) for all polymerizations in which MgBu$_2$ was used as activation reagent.

Figure 3:
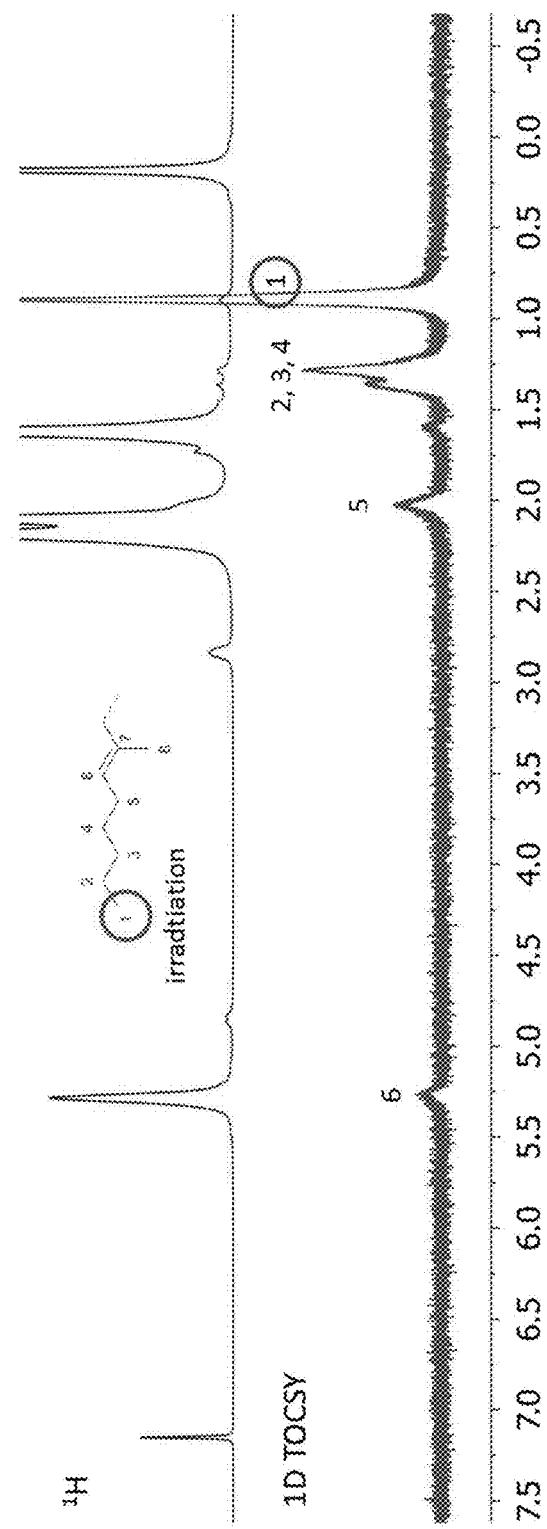
FIG. 3: $^1$H and 1D-TOCSY NMR spectra of a copolymer synthesized from isoprene and comonomer 3, showing the connectivity of the butyl chain and the poly(isoprene) backbone (Table 1-A, entry 10, recorded at 27° C. in $C_6D_6$). Irradiation at 1 (250 ms mixing time) results in excitation of signals 2, 3, 4, 5, and even 6 by magnetization transfer through bonds, proving the attachment of the butyl moiety to the PIP-backbone.

A detailed NMR analysis to prove the presence of a butyl group as chain-end was performed for a copolymer synthesized from IP and 3. TOCSY irradiation at the resonance of the CH$_3$ group results in magnetization transfer along the residual butyl chain up to the aliphatic and olefinic signals of the first isoprene unit in the backbone (FIG. 3). This outcome was further substantiated by DOSY-NMR, also showing the attachment of the butyl moiety to the PIP backbone.

Example 5

Having established the possibility to introduce a chain-end by transferring an organic group from Mg to Nd, we engaged in the synthesis of different polar functionalized organo-Mg compounds (Chart 2).

Chart 2: Polar Functionalized Organo-Magnesium Compounds Used for the Activation of Nd-Based Catalyst Systems.

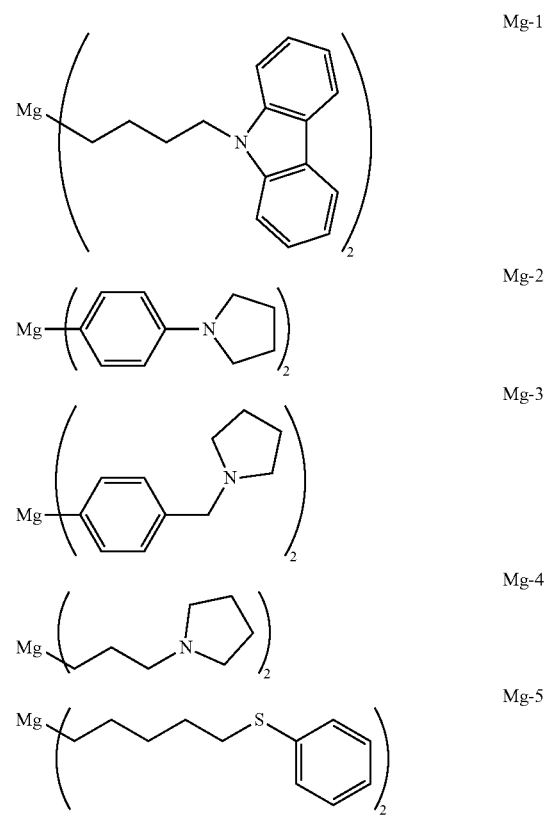

Polar functionalized organo-Mg compounds Mg-1 to Mg-5 were synthesized by reacting the according Br- or Cl-compound, e.g. Cl—C$_5$H$_{10}$—SPh for Mg-5, with activated Mg to form the mono-alkyl Mg compound ClMg—C$_5$H$_{10}$—SPh. The di-alkyl Mg compound Mg(C$_5$H$_{10}$—SPh)$_2$, Mg-5, was then formed by shifting the Schlenk equilibrium towards MgR$_2$/MgCl$_2$ upon addition of dioxane. Removal of MgX$_2$ gave the desired magnesium compounds Mg-1 to Mg-5 in good to high yields with the saturated species, e.g. C$_5$H$_{11}$—SPh, as a side product. There is no need, however, to remove the saturated species because they have no adverse influence on the intended use of the synthesized organo-Mg compounds.

Example 6

Polymerizations with a Nd:diene ratio of ca. 1:100 were performed to assess the general ability of Mg-x (x=1-5) to activate $Nd(BH_4)_3 \cdot (THF)_3$ for the trans-selective diene polymerization. The low Nd:diene ratio was chosen to ensure an end-group to backbone ratio sufficiently high for subsequent NMR analyses. Activation of $Nd(BH_4)_3 \cdot (THF)_3$ was successful with all different polar functionalized organo-Mg compounds. This includes not only the activation by Mg-alkyl compounds (Mg-1, Mg-4, and Mg-5) but also the activation by Mg-aryl compounds (Mg-2 and Mg-3).

Chain-end functionalization proceeds efficiently for the obtained polymers. It is known that each activator $MgR_2$ transfers one moiety to the Nd center in the activation step. Moreover, MALDI-TOF analyses of the obtained polymers have proved that all polymer chains bear a chain-end with R-groups derived from the $MgR_2$ used. Under the assumption of quantitative chain-end functionalization, it is possible to determine the activation efficiency of the different Mg-x (Table 2). The activation efficiency is the ratio of the amount of functional groups found in the functionalized polymers to the theoretically expected amount of functionalization expected for quantitative activation of $Nd(BH_4)_3 \cdot (THF)_3$, i.e.

TABLE 2

Results of diene polymerizations activated with polar functionalized organo-magnesium compounds.

| entry | Nd [μmol] | diene [mmol] | time [h] | activation reagent | activation efficiency[a] [%] | yield [mg] (%) | funct. groups in polymer[b] [mol %] | $M_n$[c] [$10^3$ g mol$^{-1}$] | $M_w/M_n$[c] | 1,4-trans-content[d] [%] |
|---|---|---|---|---|---|---|---|---|---|---|
| 1[e] | 60 | 6 IP | 2.5 | Mg-1 | 94 | 373 (91) | 1.5 | 10.8 | 3.2 | 93 |
| 2 | 20 | 2 IP | 2.5 | Mg-1 | 92 | 116 (85) | 1.1 | 7.4 | 1.8 | 93 |
| 3 | 60 | 6 IP | 5 | Mg-2 | n.d.[f] | 324 (79) | n.d.[f] | 16.5 | 2.8 | 92 |
| 4 | 60 | 6 IP | 5.5 | Mg-3 | 42 | 350 (86) | 0.5 | 18.8 | 4.8 | 91 |
| 5 | 50 | 4.6 BD | 5 | Mg-3 | 58 | 140 (56) | 1.1 | n.d. | n.d. | 94 |
| 6 | 50 | 5 IP | 72 | Mg-4 | 42 | 282 (83) | 0.5 | 14.2 | 4.1 | 95 |
| 7 | 50 | 4.6 BD | 3 | Mg-4 | 32 | 106 (43) | 0.8 | 17 | 2.4 | 93 |
| 8 | 50 | 4.6 BD | 5 | Mg-5 | 92 | 112 (45) | 2.2 | 5.1 | 1.8 | 94 |
| 9 | 5 | 4.6 BD | 5 | Mg-4 | n.d.[g] | 150 (60) | n.d.[g] | 57 | 2.8 | 95 |
| 10 | 5 | 4.6 BD | 5 | Mg-5 | n.d.[g] | 185 (74) | n.d.[g] | 48 | 3.0 | 94 |

Polymerization conditions: $Nd(BH_4)_3 \cdot (THF)_3$:$MgR_2$=1:1, T=60° C. in toluene or $C_6D_6$ a) activation efficiency= (funct. groups in polymer in mol %·100$^{-1}$)·$(n(MgR_2) \cdot M(diene) \cdot m(polymer)^{-1})^{-1}$ b) determined by $^1H$ NMR b) determined by GPC in THF vs. PS standards. d) determined by $^{13}C$ NMR e) Nd:MgR=1:1.5 f) not determined because signals of functional groups are (partially) overlapped by backbone signals g) not determined because the low amount of functional groups does not allow for a reliable integration.

Figure 4:
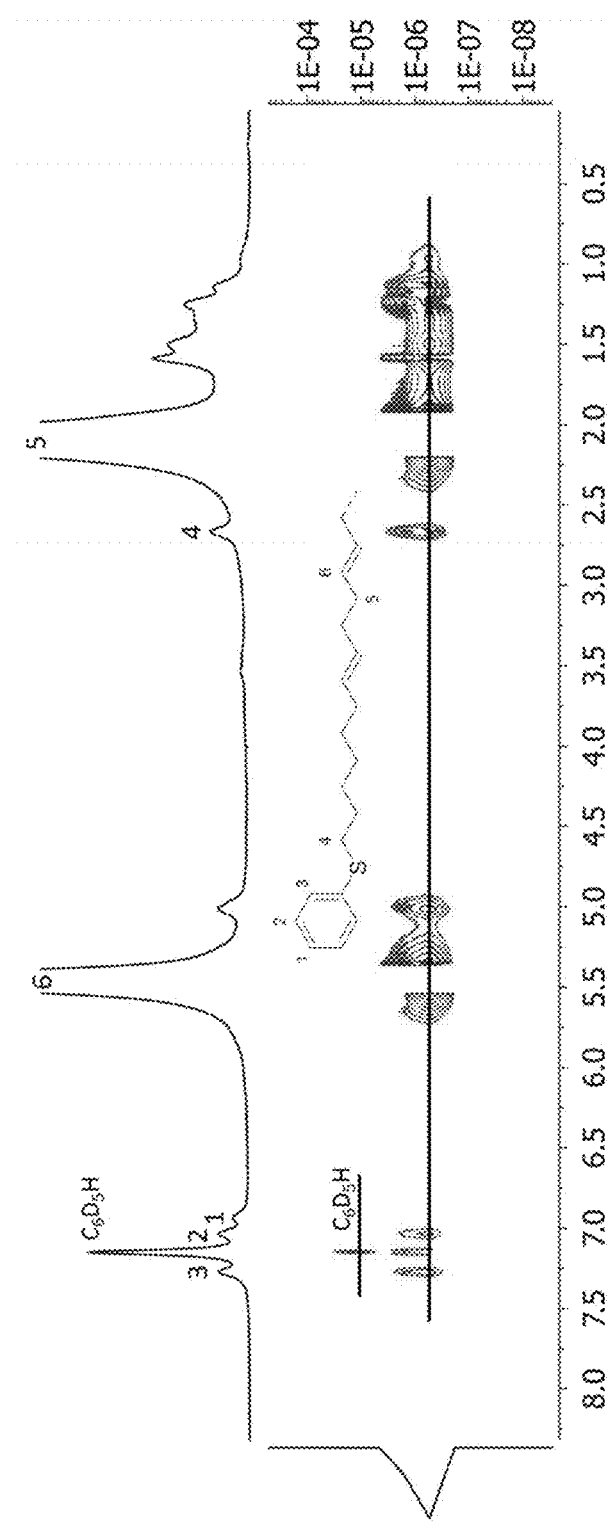
FIG. 4: $^1$H NMR spectrum and according DOSY NMR traces of chain-end functionalized poly(butadiene) sample. The sample was obtained by a polymerization activated with Mg-5 (Table 2, entry 8, spectra recorded at 27° C. in $C_6D_6$).

$^{13}C$-NMR shows all obtained polymers to be stereoregular with a high 1,4-trans-content (91-95 mol % trans-units), comparable to the model polymers obtained by activation of $Nd(BH_4)_3 \cdot (THF)_3$ with $MgBu_2$. NMR experiments verify the ability of this approach to generate polar functionalized chain-ends. All obtained polymers exhibit in both, $^1H$ and $^{13}C$ NMR, characteristic signals for the respective functional group, including pyrrolidine rings for Mg-2, Mg-3, and Mg-4, resonating between δ=2.94 ppm ($^{13}C$: 47.5 ppm, Mg-2) and 2.38 ppm ($^{13}C$: 54.1 ppm, Mg-3). In addition, signals for the benzylic protons of Mg-3 ($^1H$: 3.53 ppm, $^{13}C$: 61.1 ppm) and $(C_4H_8)N-CH_2$ group of Mg-4 are found in the respective spectra. In the case of the PhS—$CH_2$— group, introduced by activation with Mg-5, a proton signal at δ=2.67 ppm ($^{13}C$: 33.3 ppm) suggests functionalization and 1D-TOCSY reveals the connectivity along the residual pentyl-chain to the olefinic signal of the first unit in the PBD backbone. To further prove the chain-end functionalization, i.e. the attachment to the polymer chain, DOSY NMR experiments were performed for all different functional groups (FIG. 4). This verified a chain-end functionalization by showing that the functional groups have the same diffusion coefficients as the polymer backbone.

$$\text{activation efficiency} = \frac{\text{mol \% (funct. groups in polymer)}}{\text{mol \% (max. theoret. amount of funct. groups in polymer)}}$$

with mol % (max. theoret. amount of funct. groups in polymer) =

$$\frac{mmol(Mg-x)}{mg(\text{polymer yield})/mg\, mmol^{-1}(diene\, monomer)}$$

Activation occurs moderately for Mg-3 and Mg-4 with efficiencies between 42 and 58% (Mg-3) and 32 and 42% (Mg-4), respectively. In contrast, excellent activation efficiencies are observed for polymerizations activated with Mg-1 or Mg-5 (92-94%).

The molecular weight distributions are broader in these examples than observed for polymerizations activated with $MgBu_2$, this arises most likely from a slower activation compared to activation by $MgBu_2$ caused by the addition of Mg-x as a solid (the Mg-x used are typically poorly soluble in toluene). Nevertheless, molecular weights comparable to polymerizations activated with $MgBu_2$ can be obtained by adjusting the diene:Nd ratio. Polymerizations with a diene:Nd ratio of 920:1 gave polymers with molecular weights (48 and 57×103 g mol$^{-1}$) close to the theoretical value (50×103 g mol$^{-1}$, Table 2, entries 9 and 10).

Example 7

We have established separately that all three methods to functionalize the synthesized stereoregular poly(dienes) work. Further, it would be highly desirable to combine all three functionalization methods in one polymerization. This could give access to stereoregular, hetero-telechelic poly(dienes) bearing three different functional groups (Scheme 3).

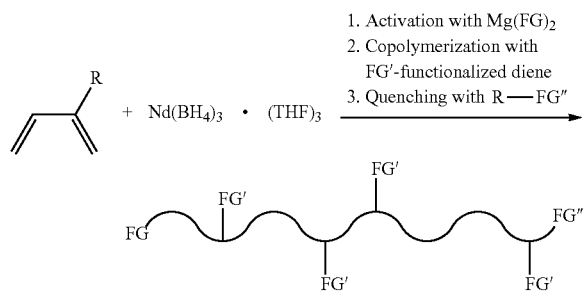

Scheme 3: Combination of three different methods for the introduction of functional groups, thus enabling the synthesis of triple functionalized, hetero-telechelic poly(dienes).

Trifunctional Polymers

Having established the functionalization of both end-groups and of the polymer backbone separately, we studied the combination of all three methods simultaneously to obtain hetero-telechelic, mid-chain functionalized poly(dienes).

Figure 5:
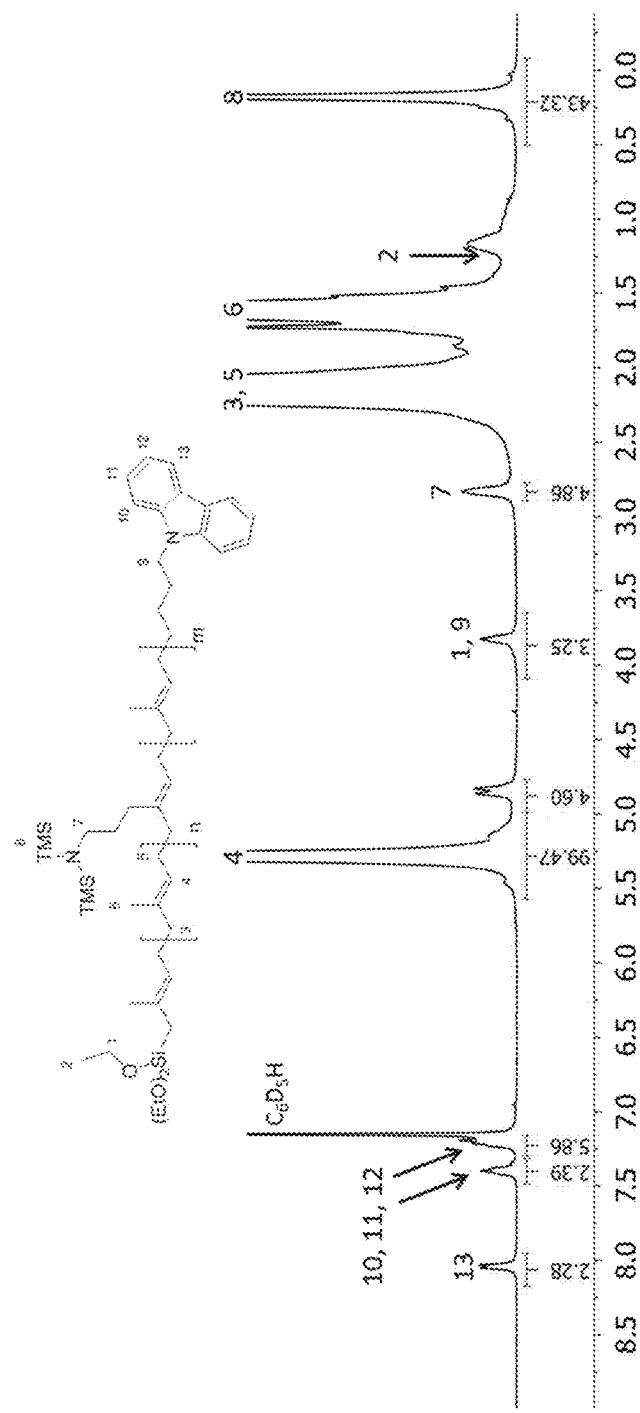
FIG. 5: $^1$H NMR spectrum of a trifunctionalized, hetero-telechelic poly(isoprene) sample (recorded at 27° C. in $C_6D_6$).

As an example of a stereoregular poly(isoprene), the copolymerization of IP and 3 was investigated. The polymerization was activated with Mg-1 (IP:Nd:Mg=100:1:1) and quenched with Si(OEt)$_4$. The obtained polymer is stereoregular with 94% 1,4-trans-units. $^1$H-NMR shows the presence of TMS-groups (0.19 ppm) and TMS$_2$NCH$_2$-groups (2.84 ppm) indicating a comonomer incorporation of 2.3 mol %. CarbNCH$_2$-groups resonate at 3.83 ppm and the aromatic protons of the carbazyl group are clearly observed (FIG. 5). The presence of 1 mol % of CarbN-groups derived from Mg-1 agrees excellently for the expected theoretical degree of functionalization (1 mol %) when quantitative chain-end functionalization is considered for the targeted degree of polymerization DP=100. 2D NMR-spectroscopy also reveals the presence of (EtO)$_3$Si-groups. While the proton resonance of the SiOCH$_2$CH$_3$ group is overlapped by the resonance of CarbNCH$_2$-groups (3.83 ppm), the presence of a signal at 59.0 ppm in the $^{13}$C dimension of the HSQC spectrum proves the functionalization of the other chain-end. However, as already observed in the quenching experiments above, the degree of functionalization is moderate (ca. 15-20% of the polymer chains). The connection of all three different functional groups to the polymer backbones was additionally verified by DOSY NMR.

Example 8

Figure 6:
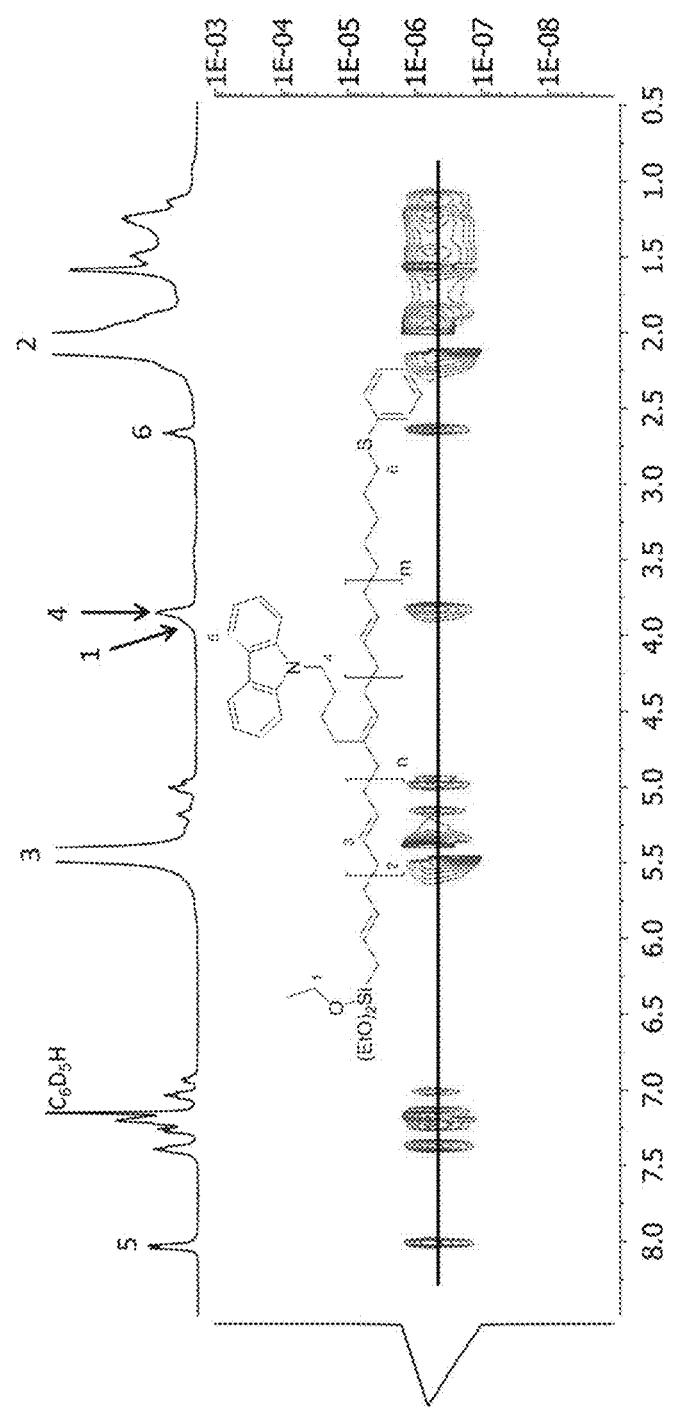
FIG. 6: $^1$H NMR spectrum and according DOSY NMR traces of a trifunctionalized, hetero-telechelic poly(butadiene) sample, proving the connection of all different functional groups to the polymer backbone (recorded at 27° C. in $C_6D_6$).

As an example of a stereoregular poly(butadiene), a copolymerization of BD and 6 (2 mol %) was studied. The polymerization was activated by Mg-5 (BD:Nd:Mg=100:1:1) and quenched with Si(OEt)$_4$ at the end of the reaction. $^1$H, $^{13}$C, and 2D NMR spectroscopy shows the polymer obtained to be stereoregular (94% 1,4-trans-units) and reveals the presence of all three different functional groups (FIG. 6): PhS— groups originate from the activation of Nd(BH$_4$)$_3$·(THF)$_3$ with Mg-5 ($^1$H: 2.66 ppm, $^{13}$C: 33.2 ppm for PhS—CH$_2$-groups). Carbazol moieties (CarbN) introduced by direct copolymerization with 6 show characteristic shifts in the aromatic region (e.g. $^1$H: 8.04 ppm, $^{13}$C: 120.5 ppm) and at 3.84 ppm ($^{13}$C: 42.5 ppm) for CarbN-CH$_2$-groups. As already observed in the example above, the most characteristic proton resonance of the SiOCH$_2$CH$_3$ group (3.90 ppm) is (partially) overlapped by the resonance of CarbNCH$_2$-groups, but the presence of SiOCH$_2$CH$_3$-groups is proven by 2D NMR spectroscopy ($^{13}$C: 59.0 ppm for SiOCH$_2$CH$_3$). A connectivity between all three different functional groups and the polymer backbone was unambiguously established by DOSY NMR (FIG. 6).

Example 9

We have shown in previous work, that the direct copolymerization of functionalized dienes with butadiene or isoprene is feasible with cis-selective Nd-based catalyst systems. It would also be highly desirable for these systems to introduce the possibility of functionalizing chain-ends by activation with functionalized activators. Prior examples of the initiation of cis-selective butadiene polymerizations with magnesium alkyls are scarce. We tested the reported catalyst system (Nd(versatate)$_3$ activated with MgR$_2$ in the presence of ethylaluminium sesquichloride) in polymerizations of butadiene after activation with MgBu$_2$ or Mg-5. Polymerizations activated with MgBu$_2$ showed that the used catalyst system can produce stereoregular poly(butadiene) with a high content of 1,4-cis-units (e.g. 92 mol %). Similarly, a BD polymerization activated with Mg-5 resulted in the formation of stereoregular PBD (86 mol % 1,4-cis-units). Additionally, NMR spectroscopy reveals the presence of functional groups introduced by the activation with Mg-5 as already described above for trans-selective catalyst systems. These results evidence that the introduction of functionalized chain-ends by usage of functionalized activators is also feasible in cis-selective diene polymerization catalyzed by Nd-based catalyst systems.

What is claimed:

1. A method of making a functionalized elastomer, comprising the step of:
polymerizing a conjugated diene monomer in the presence of a lathanide-based coordination polymerization catalyst activated with a magnesium compound of formula 1

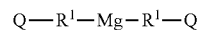

where R$^1$ is phenylene, or a linear or branched alkane diyl group containing 2 to 10 carbon atoms, or a combination of one or more phenylene groups and one or more linear or branched alkane diyl groups containing 1 to 10 carbon atoms;

Q is of formula 2 or 3

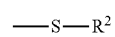

where R$^2$ is phenyl, or a linear or branched alkyl group containing 2 to 10 carbon atoms; and

where $R^3$ and $R^4$ are independently phenyl or a linear or branched alkyl group containing 1 to 10 carbon atoms, or $R^3$ and $R^4$ taken together with the nitrogen atom represent a nitrogen containing heterocyclic group containing from 4 to 12 carbon atoms.

2. The method of claim 1, wherein the magnesium compound of formula 1 is selected from the group consisting of

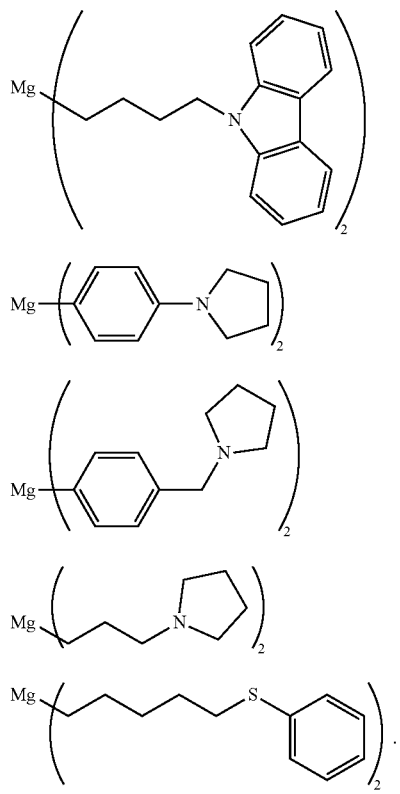

3. The method of claim 1, wherein the lanthanide-based catalyst is selected from neodymium borohydride complexes and neodymium carboxylates.

4. The method of claim 1, wherein the lanthanide-based catalyst comprises $Nd(BH_4)_3 \cdot (THF)_3$.

5. The method of claim 1, wherein the conjugated diene monomer is selected from the group consisting of 1,3-butadiene, isoprene, 2,3-dimethyl-1,3-butadiene, piperylene, 3-butyl-1,3-octadiene, and 2-phenyl-1,3-butadiene.

6. The method of claim 5, wherein the monomer further comprises a functionalized monomer of formula 4

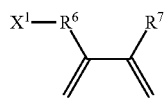

wherein $R^6$ is a covalent bond, phenylene, a linear or branched alkane diyl group containing 1 to 10 carbon atoms, or a combination of one or more phenylene groups and one or more linear or branched alkane diyl groups containing 1 to 10 carbon atoms; $R^7$ is hydrogen or a linear or branched alkyl group containing 1 to 10 carbon atoms; $X^1$ is selected from formulas 5 and 6

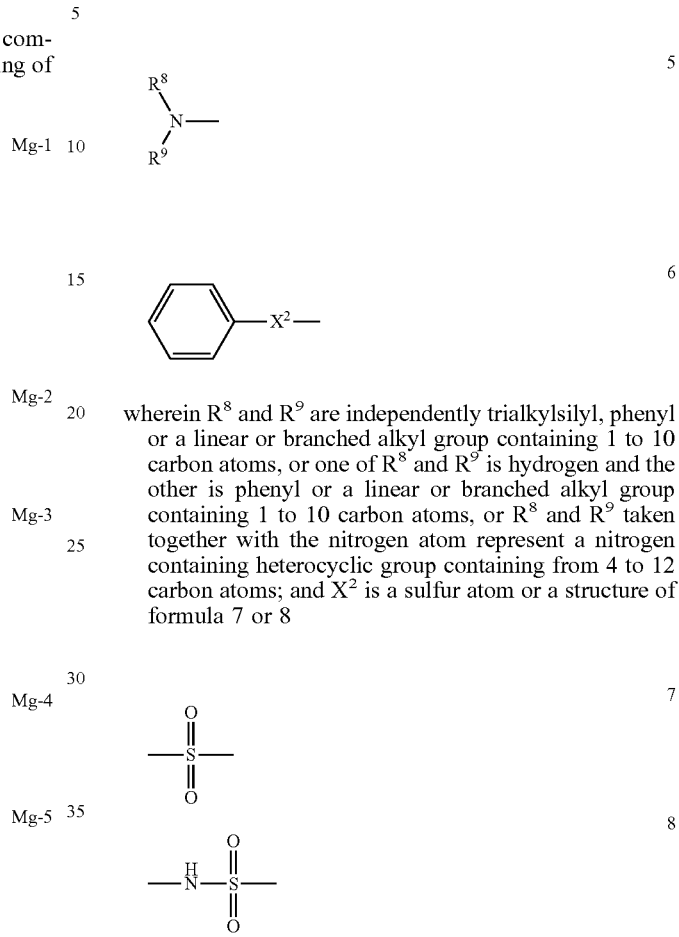

wherein $R^8$ and $R^9$ are independently trialkylsilyl, phenyl or a linear or branched alkyl group containing 1 to 10 carbon atoms, or one of $R^8$ and $R^9$ is hydrogen and the other is phenyl or a linear or branched alkyl group containing 1 to 10 carbon atoms, or $R^8$ and $R^9$ taken together with the nitrogen atom represent a nitrogen containing heterocyclic group containing from 4 to 12 carbon atoms; and $X^2$ is a sulfur atom or a structure of formula 7 or 8 wherein when $X^2$ is of formula 8, the S atom of formula 8 is adjacent to the phenyl ring of formula 6 and the N atom of formula 8 is adjacent to $R^6$.

7. The method of claim 1, further comprising the step of terminating the polymerization with a functional terminator substituted with a functional group comprising at least one heteroatom selected from phosphorus, boron, oxygen, halogens and silicon.

8. The method of claim 7 wherein the functional terminator comprises at least one functional group selected from the group consisting of phosphane, phosphonic acid, phosphate, phosphodiester, phosphotriester, silyl, alklysilyl, alkoxysilyl, and siloxy.

9. The method of claim 7, wherein the functional terminator comprises a terminator selected from the group consisting of tetraethoxysilane, n-octyltriethoxysilane, 3-chloropropyltriethoxysilane, and chlorodiphenylphosphine.

10. The method of claim 1, wherein the nitrogen containing heterocyclic group is selected from the group consisting of the structures.

* * * * *